United States Patent [19]

Weir et al.

[11] Patent Number: 5,204,922
[45] Date of Patent: Apr. 20, 1993

[54] OPTICAL SIGNAL CHANNEL SELECTOR

[75] Inventors: Charles S. Weir, San Diego; Karl H. Weise, Valley Center, both of Calif.

[73] Assignee: Puritan-Bennett Corporation, Carlsbad, Calif.

[21] Appl. No.: 780,477

[22] Filed: Oct. 22, 1991

[51] Int. Cl.$^5$ ............................................. G02B 6/26
[52] U.S. Cl. ................................... 385/18; 385/19; 385/25; 356/419
[58] Field of Search ............... 385/18, 19, 22, 25; 356/406, 416, 419

[56] References Cited

U.S. PATENT DOCUMENTS

| Re. 31,879 | 5/1985 | Lubbers et al. | 436/133 |
|---|---|---|---|
| 3,667,850 | 11/1970 | Smith et al. | 356/419 |
| 4,399,099 | 8/1983 | Buckles | 422/58 |
| 4,476,870 | 10/1984 | Peterson et al. | 128/634 |
| 4,580,059 | 4/1986 | Wolfbeis et al. | 250/459.1 |
| 4,907,857 | 3/1990 | Giuliani et al. | 350/96.29 |
| 4,938,555 | 7/1990 | Savage | 385/18 |
| 5,015,098 | 5/1991 | Berg et al. | 356/419 |

OTHER PUBLICATIONS

Optical Fluorescence and Its Application to an Intravascular Blood Gas Monitoring System, Gehrich, et al., Feb. 1986.

Primary Examiner—John D. Lee
Assistant Examiner—S. W. Barns
Attorney, Agent, or Firm—Fulwider, Patton, Lee & Utecht

[57] ABSTRACT

The optical signal channel selector apparatus includes one or more first optical channels, and a plurality of a secondary optical channels for carrying an optical signal. A parabolic mirror is rotatable to provide optical communication between a first optical channel and any one of the secondary optical channels. A position encoded stepper motor is coupled to the parabolic mirror for controlling the position of the mirror. Solid state optical interface blocks having one or more filters receive the optical signal and transmit output optical signals with filtered wavelength ranges in the secondary optical channels. The rotation of the mirror by a position encoded stepper motor allows selection of a desired secondary channel, and automatically shutters the remaining channels closed.

35 Claims, 3 Drawing Sheets

OPTICAL SIGNAL CHANNEL SELECTOR

BACKGROUND OF THE INVENTION

1. Field of the Invention

This invention is directed generally to optical signal channel selector apparatus for instrumental analysis systems utilizing multiple channels for carrying optical signals and more particularly relates to an optical signal channel selector apparatus adapted for use in a multiple optical fiber sensor system.

2. Description of Related Art

Optomechanical systems for transmitting optical signals are well known in the art and include general classes of optical elements such as light reflectors, light filters, lenses, and optical fibers. Although optical signals from laser sources have been used in telecommunications to carry vast amounts of information over optical signal channels for great distances, optical signals of broader ranges of light wavelengths have also recently been used in optical fiber based analyte sensors employing light absorbance dye indicators or fluorescent dye indicators.

Heretofore in analytical instruments employing optical fibers to carry multiple optical signals, switching between uses of an optical channel as an input signal channel transmitting one wavelength range of light and an output signal channel transmitting a different wavelength range of light has generally been accomplished by pulsing input signals and mechanically interfacing the optical channel with one or more optical filter blocks, which typically involved a mechanical arrangement of solenoids or stepper motors for manipulation of the necessary optical elements for transmission of selected wavelengths of light to be transmitted or detected. Problems such as optical switching noise due to oscillation of moving optical elements which reciprocate or move in shutter action, problems in sticking and misalignment of reciprocating or rotating filter element, and cross-talk between channels associated with this type of mechanical switching of optical interface elements can give rise to reduced signal to noise ratios and can generally interfere with the performance of the instrument.

A fluorescent indicator typically utilizes light in one wavelength region to excite the fluorescent indicator dye to emit light of a different wavelength. Such a sensor may for example utilize a single dye that exists in an acid form and a base form, each with a different excitation wavelength.

Extremely fine sensors with multiple optical fibers for carrying excitation signals to a single sensor head and for carrying return fluorescence emission signals from the sensors have now been constructed for in vivo, intravascular monitoring of multiple vital signs of a patient. Heretofore, each type of sensor typically required its own optical fiber or set of optical fibers for carrying excitation and emission signals. Although a single broad spectrum light source can be used for each of the different types of sensors in a multiple optical fiber sensor by rapidly switching optical filters in optical interface blocks to provide an appropriate wavelength range for each type of requisite excitation signal, such switching of optical elements has been cumbersome, slow, and often not precisely aligned.

Blood gas and blood pH analyzers employing multiple optical fiber sensors have been hindered by problems associated with switching filters in a filter wheel or channel switching in optical interface blocks which include solenoids, or other types of linear actuators, or stepper motors for filter wheels, for mechanically switching between the optical channels as different blood parameters are monitored. In such systems, one or more optical channels can be used to transmit an optical signal from a source to the optical fiber sensor, and to convey return signals from the sensor placed within the vasculature of a patient to an optical detector unit to monitor one or more analytes of interest.

Typically, selection of input signals has also involved the mechanical switching of excitation filters at an optical interface between a light source and the optical fiber sensor, and selection of output signals has involved a similar mechanical switching of emission filters at an optical interface between the optical fiber sensor and a detector. Where the same optical fibers are used to carry both input and output optical signals to and from the sensors, pulsing of the input excitation signal allows for the detection of the output emission signal between excitation pulses. Interference of input and output signals within the optical interface blocks during switching, cross-talk between channels, and signal noise associated with the moving parts in the optical blocks, can reduce the accuracy and reliability of blood parameter measurements from such multiple optical fiber sensor systems.

To reduce the incidence and severity of these problems it would be desirable that an optical signal channel selector be provided which closes non-selected optical channels to avoid cross-talk of the optical signals and to reduce signal noise, and that optical interface blocks associated with individual optical fibers have no moving parts. Such an optical signal channel selector would allow the speed of the instrumental analysis to be limited by the analyte sensing method rather than the switching speed of the system, and such solid state optical blocks could be made smaller and with fewer components at reduced cost.

SUMMARY OF THE INVENTION

Briefly, and in general terms, the present invention provides for an optomechanical optical signal channel selector apparatus for a multiple optical sensor system, including a first optical channel, and a plurality of second optical channels for carrying an optical signal. A channel selector means is adapted to be movable, and thus be in optical communication between a first optical channel and any one of the second optical channels arrayed about the channel selector. The channel selector is preferably a rotatable parabolic mirror rotatably driven by a position encoded stepper motor connected coaxially with the mirror.

The channel selector mirror preferably can be turned to focus the optical signal received from a source disposed in the axis of rotation of the mirror to any one of a plurality of the secondary optical channels disposed in a circle about the mirror. This arrangement allows any channel of an optical fiber based blood gas analyzer to be accessed quickly, automatically shutters the unselected secondary channels closed and allows close control of the signal transmission time for each selected secondary channel.

A solid state optical interface block having one or more filters for receiving the source optical signal and transmitting output optical signals with filtered wavelength ranges is preferably provided in the second optical channels. In one preferred embodiment, the secondary channel includes an optical interface block having a plurality of filters for receiving the source optical signal and transmitting a plurality of output optical signals with different wavelength ranges, and means for combining the plurality of output optical signals. The switching function is advantageously performed outside optical interface blocks provided for filtering and making optical signal connections, allowing the optical blocks to be configured with no moving parts, thereby reducing noise and cross-talk between channels.

In the method of the invention, the concentration of one or more analytes in a sample may be measured utilizing the optical signal transmission and detection system of the invention. According to the method of the invention, one or more sensor elements are exposed to a sample containing the analyte constituents to be measured. A source optical signal is generated and transmitted from a first optical channel by the channel selector to one of the second optical channels through a solid state optical interface block to transmit a filtered excitation optical signal with a limited wavelength range to one of the sensor elements. A first output detection signal from the sensor element receiving the excitation signal can then be measured. For a single excitation sensor requiring only one excitation signal, the concentration of the first analyte in the sample can be determined based upon this output detection signal. After the first excitation signal is sent to a sensor, the channel selector can then be rotated to transmit the source optical signal from the first optical channel to another of the second optical channels through a solid state optical interface block to transmit a second filtered excitation optical signal with a limited wavelength range to one of the sensor elements, which may be a different sensor in the case of a single excitation sensor, or which may be the same sensor element in the case of a dual excitation sensor. The second output detection signal from the sensor element receiving the second excitation signal can then be measured. Where the first sensor is a dual excitation sensor, the first and second excitation signals can be sequentially directed to the first sensor, and the concentration of the analyte can be determined from the first and second output detection signals from the first sensor. Where the first and second sensors to which the first and second excitation signals are directed are single excitation sensors, the concentration of two different analytes can be determined from the output detection signals from the first and second sensors. In this manner, the pH, and the partial pressures of oxygen and carbon dioxide in a patient's blood can be determined. The rotational position of the channel selector about its axis can be controlled to communicate the optical signal between the first optical channel means and sequential ones of the second optical channel means. For example, the stepper motor used for rotating the channel selector can be controlled by generating and sending the stepper motor encoded signals of the desired rotational position of the channel selector mirror about its axis.

These and other aspects and advantages of the invention will become apparent from the following detailed description, and the accompanying drawings, which illustrate by way of example the features of the invention.

DETAILED DESCRIPTION OF A PREFERRED EMBODIMENT

Figure 1:
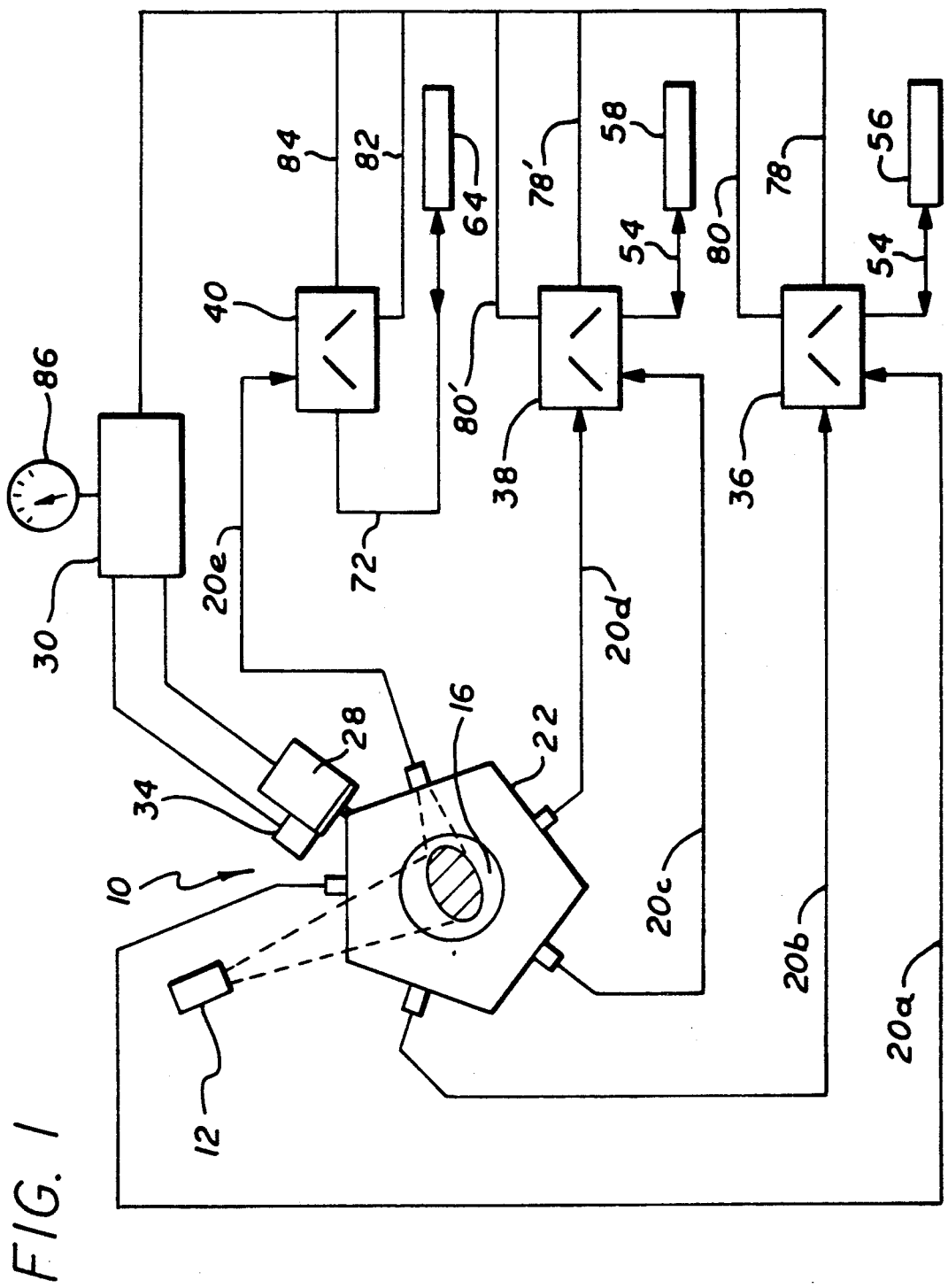
FIG. 1 is a schematic of the optical signal channel selector configured for use in a multiple analyte sensor system.
Figure 2:
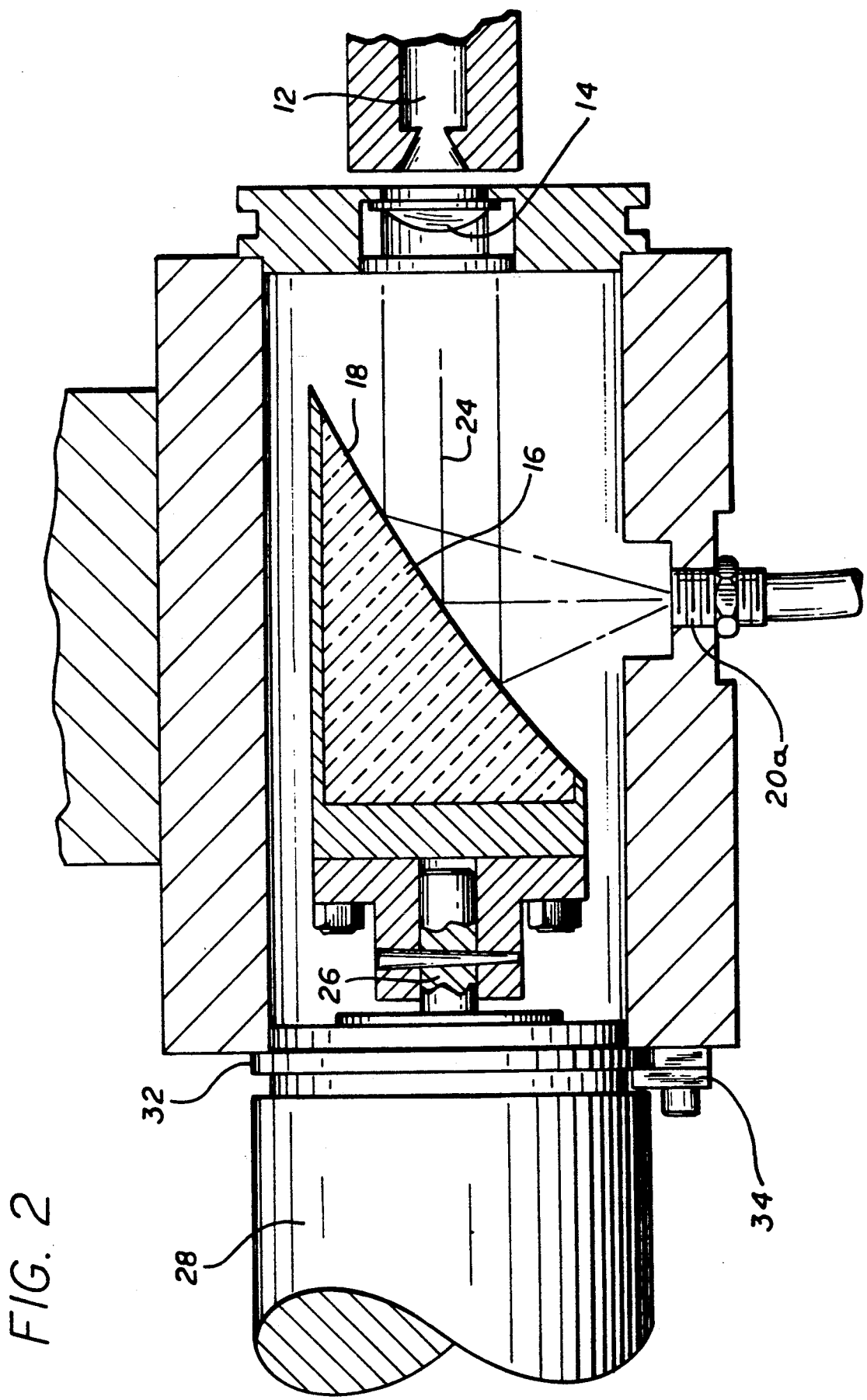
FIG. 2 is an elevational view of the channel selector of the invention.

As is shown in the drawings for purposes of illustration, the invention is embodied in an optomechanical optical signal channel selector apparatus for a multiple optical sensor system which can substantially reduce signal interference, cross-talk, and signal noise in optical signal channels normally associated with moving parts in optical interface blocks switching between channels The channel selector system can increase the accuracy and reliability of blood parameter measurements in multiple optical fiber sensor systems such as those having a source optical channel, and a plurality of second optical channels for carrying an output optical signal.

The type of sensors contemplated for use with the optical signal channel selection apparatus of the invention typically utilize the phenomenon of fluorescence of a dye material when excited by an input optical signal of a desired wavelength range. Such systems generally incorporate a dye matrix applied to the tip of an optical fiber, and a selected wavelength of light which is transmitted over the optical fiber to excite the dye to fluoresce. The return fluorescence signal can travel back over the same optical fiber to be measured by a photodetector. The emissions from the dye are commonly at a frequency different from that used for excitation, and the intensity of the fluorescence of the dye measured by the detector is a function of the amount of the fluorescing species of the analyte being measured in the sample. In this way the oxygen, carbon dioxide and pH content of a patient's blood can be monitored.

Optical pH sensors typically include a fluorescent indicator dye, such as fluorescein or hydroxypyrenetrisulfonic acid (HPTS). The dye is typically capable of existing in two forms, an anionic or base form, and a protonated or acid form. The two forms are each excited by different frequencies which can be carried to the sensor by separate optical signal channels, or can be combined to be carried over a single channel. The two forms fluoresce at the same frequency, which can be carried over a single channel. The intensity of the output signal is proportional to the pH of the sample to which the sensor is exposed, and can thus be used to determine pH of the sample.

The concentration of carbon dioxide in a solution can similarly determined by an optical sensor by measuring the pH of a solution of bicarbonate in equilibrium with the carbon dioxide in the solution. The bicarbonate and carbon dioxide form a pH buffer system in which the hydrogen ion concentration generally varies with the carbon dioxide concentration. The carbon dioxide content of a solution may, for example, be measured with a fiber optic sensor utilizing fluorescein or HPTS.

A sensor for measuring the partial pressure of oxygen may, for example, include the placement of two dyes with differing oxygen sensitivities in a polymer matrix.

The two dyes may have the same general range of wavelength excitation frequencies, but distinctly different ranges of emission frequencies. Appropriate dye indicators for use in such an oxygen sensor probe include coronene and decacyclene. Coronene and decacyclene dye indicators can both be excited at 366 ±20 nm, and the fluorescence emissions from these two dye indicators are approximately 430 ±20 nm and approximately 520 ±25 nm, respectively. Thus, a single optical channel may be used to carry a single excitation signal to the sensor and to carry the two return emission signals from the sensor for analysis.

As is shown in FIG. 1, the optical channel selector system 10 preferably includes a primary optical signal channel, which can for example comprise a flashlamp optical signal source 12 which provides pulses of a broad spectrum of light, and accompanying optics, such as a lens 14 for focusing or collimating the source optical signal. The optical signal is, in this embodiment, directed from the primary optical signal channel to a channel selector means, which is preferably a parabolic mirror 16, mounted for rotation about an axis 18 for reflecting the optical signal sequentially to one of a plurality of secondary optical channels disposed in a circle about the mirror, in a plane normal to the axis of rotation of the mirror. The optical signal source may include an intermediate input optical signal channel such as an optical fiber, a mirror, or the like, operating to direct a light signal toward the channel selector. The parabolic focusing reflective surface 18 is preferably disposed at an angle incident to the incoming optical signal so as to direct the signal to one of a plurality of secondary optical signal channels, such as carrier optical fiber leads 20abcde mounted in a housing 22 about the mirror.

The rotatable parabolic mirror is mounted for rotation about an axis 24 which is coaxial with the shaft 26 of a stepper motor 28 to which the mirror is coupled. The stepper motor thus incrementally drives the shaft to rotate the mirror, typically in steps of 1.8 degrees. The stepper motor is also preferably electrically connected to a control unit 30, such as an IBM PC used as a computer controller to drive the stepper motor, for controlling the rotational position of the mirror to direct the optical signal from the flashlamp source to any one of the optical fiber leads disposed about the mirror. The control unit preferably rotates the mirror sequentially from one optical fiber lead to the next, pausing at each optical fiber channel for a desired amount of exposure time. Means for encoding the rotational position of the mirror are also preferably electrically connected with the computer control unit to provide feedback to the control unit, to correct any errors in the positioning of the mirror which may occur. Thus, for example, an encoder disk 32 may be coupled to the shaft of the stepper motor, and a position encoder detecting unit 34 for detecting position flags on the encoder disk and generating an encoded position signal when the flags are detected may be mounted adjacent to the encoder disk. The position signal provided to the computer control unit can thus be used to determine the rotational position of the mirror, as is commonly known in the art.

In the preferred embodiment shown in FIG. 1, the five optical fiber leads are each in communication with one of three solid state optical interface blocks for filtering the source optical signal and conveying it to an optical analyte sensor element which is preferably a component of a multiple optical fiber sensor (not shown), which may include pH, $pO_2$, and $pCO_2$ elements. In the context of the present invention, the term "solid state" is used to signify that the interface block has no moving parts. In this embodiment, optical fiber 20a is connected as the short wavelength input channel 1 to dual excitation optical block 36, and optical fiber 20b is connected as the long wavelength input channel 1 to the dual excitation optical block 36. Channel 20c is connected as the short wavelength input channel 2 to the second dual excitation block 38, and channel 20d is connected as the long wavelength input channel 2 to the second dual excitation block 38. Channel 20e is connected as the input channel 3 to dual emission block 40. Each optical interface block includes at least one filter for limiting the wavelength range of the source optical signal to generate an output optical signal specific to the requirements of sensors, such as pH, $CO_2$, or $O_2$ sensors, which are typically connected by a feed optical fiber to the associated optical interface block to receive the appropriately filtered optical signal.

Figure 3:
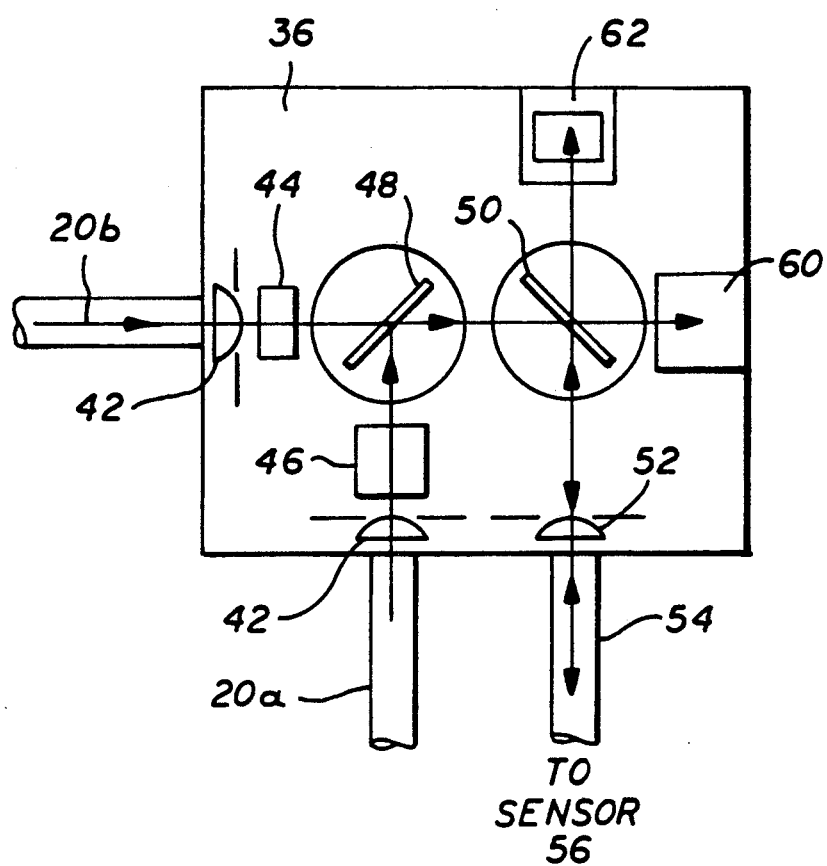
FIG. 3 is a schematic of a dual excitation optical interface block from FIG. 1.

Thus, as is shown in FIG. 3, the channel 1 optical fibers 20ab and the channel 2 optical fibers 20cd are connected to the dual excitation optical interface blocks 36 and 38 respectively to convey the source optical signal through input focusing lenses 42 and optical filters 44, 46 to generate the short and long wavelength output optical signals, respectively. The dual excitation blocks 36, 38 are essentially identical, and for the sake of simplicity, only the dual excitation block 36 receiving the channel 1 inputs will be described in detail. The dual excitation optical block 36 preferably includes a first dichroic mirror 48 disposed at an angle to the short and long wavelength outputs to simultaneously transmit the long wavelength output and reflect the short wavelength output to a second dichroic mirror 50 which functions as a combiner in reflecting both the short and long wavelength output signals through the output focusing lens 52 which focuses the combined signals to the sensor output channel optical fiber 54 connected to a pH sensor 56 or $CO_2$ sensor 58 as described above, for example. The dual excitation optical block may advantageously include an output optical signal detector 60 which receives a portion of one or both wavelengths of the combined output signal through the second dichroic mirror for determining the intensity of the combined output signal as a reference for measurements taken by the sensor. The output channel optical fiber preferably also conveys a return optical signal from the sensor 56 or 58 representing the measurement of the analyte of interest, which is focused by the objective lens 52 through the second dichroic mirror to emission signal detector 62 which measures the intensity of the return signal.

Figure 4:
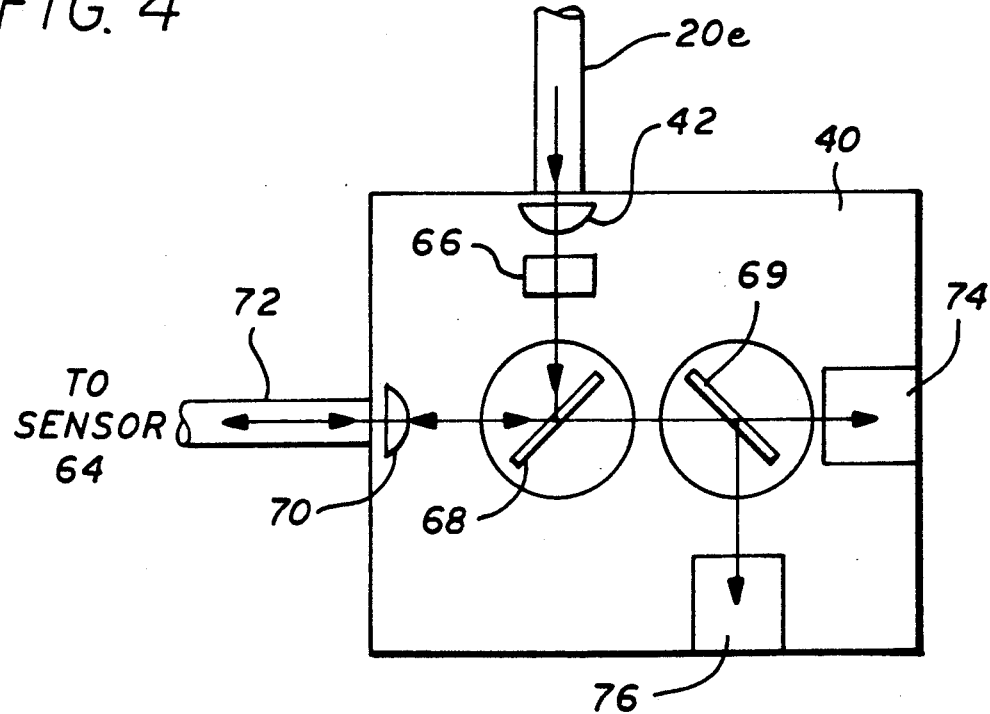
FIG. 4 is a schematic of a dual emission optical interface block from FIG. 1.

The channel 3 optical fiber 20e is preferably connected to the dual emission optical interface block 40 illustrated in FIG. 4, to convey the source optical signal to a sensor 64 such as an oxygen sensor as described above, for example. The source optical signal is transmitted from the optical fiber 20e through the input focusing lens 42 and the optical filter 66 to generate the desired wavelength range output optical signal to a first dichroic mirror 68 disposed at an angle to the filtered output signal to reflect the filtered output signal to an objective focusing lens 70 which focuses the output signal to the sensor output channel optical fiber 72 connected to sensor 64. The output channel optical fiber preferably also simultaneously conveys two return optical signals of different wavelengths from the sensor 64, from which a ratio may be determined that is indicative, for example, of oxygen partial pressure being measured. The return signals are simultaneously focused by the lens 70 through the first dichroic mirror to a second dichroic mirror 69 which serves a beam splitter, transmitting the longer wavelength signal, for example, to a long wavelength signal detector 74, and reflecting the shorter wavelength signal, for example, to a short wavelength signal detector 76, for simultaneous measurement of the respective intensities of the different wavelengths of the return signal.

The electrical outputs of the channel 1 signal detectors 60, 62, channel 2 signal detectors 60', 62' (not shown), and channel 3 signal detectors 74 and 76 are connected through cables 78, 80, 78', 80', 82, 84, respectively, to the computer control unit 30, which receives the electrical output of the detectors and determines the measurements of the blood analytes being monitored, such as pH, $CO_2$, or $O_2$. The computer is preferably programmed to measure the analyte being monitored based upon the specific measurement of fluorescence intensity represented by the electrical output signals received by the computer, according to an algorithm based upon signal outputs from measurements from samples with known analyte levels. The output of the computer may be indicated on a meter 86 or other suitable readout device.

Thus, according to the method of the invention, the concentration of a plurality of analytes in a sample may be sequentially measured utilizing the optical signal transmission and detection system of the invention. The multiple sensor elements are preferably placed in the sample, such as by placing them together in a multiple optical fiber sensor unit in the bloodstream through an introducing cathether to expose the sensor elements to the analyte constituents to be measured. A source optical signal is generated and transmitted from a first optical channel by the channel selector to a first one of the second optical channels through one of the solid state optical interface blocks to transmit an excitation optical signal with a limited wavelength range to one of the sensor elements. A first output detection signal from the sensor element receiving the excitation signal can then be measured, and in the case of a single excitation sensor, the concentration of the first analyte in the sample can be determined based upon the first output detection signal. After the first excitation signal is sent to a sensor, the channel selector is rotated to transmit the source optical signal from the first optical channel to a second one of the second optical channels through one of the solid state optical interface blocks to transmit a second excitation optical signal with a limited wavelength range to one of the sensor elements, which may be a different sensor in the case of a single excitation sensor, or, if the first sensor element is a dual excitation sensor, which may be the same sensor element for receiving the second of the two excitation pulses needed for determining sensor response in the case of a dual excitation sensor. The second output detection signal from the sensor element receiving the second excitation signal can then be measured, and in the case of a dual excitation sensor, the concentration of the analyte can be determined, based upon the first and second output detection signals. In the case where the second excitation signal is directed to a single excitation sensor element for a different analyte, the concentration of a second analyte can be determined from the second output detection signal. In this manner, for example, the pH, and the partial pressures of oxygen and carbon dioxide in a patient's blood can be determined. The rotational position of the channel selector about its axis can also be controlled to communicate the optical signal between the first optical channel means and sequential ones of the second optical channel means. The stepper motor used for rotating the channel selector can be controlled by generating and sending encoded signals of the desired rotational position of the channel selector mirror about its axis.

Although the channel selector system of the invention has been described for use with a multiple optical fiber sensor, it is apparent that the invention may also be used with a plurality of separate optical sensor elements for measuring blood pH, $pCO_2$, and $pO_2$. It should also be apparent that the optical signal channels and the channel selector mirror could alternatively be arranged so that the mirror receives optical signals from any one of a plurality of off-axis input optical channels arrayed about the channel selector mirror and directs the signals to an output optical channel aligned with the axis of rotation of the mirror, or to a plurality of off-axis output channels.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An optical signal channel selector apparatus for an optical signal transmission and detection system having multiple optical channels for communicating at least one optical signal comprising:

a) at least one first optical channel means for carrying an optical signal;

b) a plurality of a second optical channel means for carrying an optical signal, each said second optical channel means including a solid-state optical fiber block having at least one filter means for receiving said optical signal and transmitting an output optical signal with a limited wavelength range;

c) movable selector means adapted to be in optical communication with any one of said first optical channel means and movable to be in optical communication with any one of said second optical channel means for providing optical communication between one of said first optical channel means and a selected second optical channel means; and d) means for moving said selector means to provide optical communication between one of said first optical channel means and a different one of said second optical channel means.

2. The apparatus of claim 1, wherein said movable selector means includes mirror means having a reflective surface rotatable about an axis for reflecting said optical signal between said first and second optical channel means.

3. The apparatus of claim 1, wherein said mirror means comprises a parabolic focusing mirror.

4. The apparatus of claim 1, wherein said second optical channel means includes a plurality of optical fiber channels for carrying a source optical signal received from said first optical channel means to each of said optical interface block to generate an output optical signal with a limited wavelength range, said plurality of optical fiber channels being disposed about said mirror means in a plane normal to the axis of rotation of said mirror means for receiving said source optical signal reflected from said mirror means, whereby said mirror means is adapted to communicate said optical signal between said first optical channel means and sequential ones of said second optical channel means.

5. The apparatus of claim 1, wherein said selector means comprises mirror means rotatable about an axis and said means for moving said selector means includes means for controlling a rotational position about said axis to communicate said optical signal between said first optical channel means and sequential ones of said second optical channel means.

6. The apparatus of claim 5, wherein said means for moving said selector means includes a stepper motor having a rotatably driven shaft coaxial with the rotational axis of said mirror means and connected to said mirror means for aligning said mirror means with said sequential ones of said second optical channel means.

7. The apparatus of claim 5, wherein said means for controlling said rotational position includes position encoding means for generating an encoded signal representing the rotational position of said mirror means about said axis.

8. The apparatus of claim 6, wherein said means for moving said selector means includes position encoding means for generating an encoded position signal representing the rotational position of said mirror means about said axis, and computer means in electrical communication with said position encoding means and said stepper motor for receiving said encoded position to monitor the rotational position of said mirror means and to control the stepper motor responsive to said encoded position signal.

9. The apparatus of claim 1, wherein said first optical channel means comprises a broad spectrum light source for generating a source optical signal.

10. The apparatus of claim 9, wherein said first optical channel means comprises lens means for collimating or focusing said source optical signal.

11. The apparatus of claim 1, wherein said first optical channel means comprises an optical fiber for carrying said optical signal.

12. The apparatus of claim 1, wherein said second optical channel means comprises an optical fiber for carrying said optical signal.

13. The apparatus of claim 1, wherein said second optical channel means includes optical signal detector means for measuring intensity of said output signal.

14. The apparatus of claim 1, wherein said second optical channel means includes an oxygen sensor for receiving said output optical signal and generating at least one return optical signal representing an oxygen partial pressure in a sample.

15. The apparatus of claim 1, wherein said second optical channel means includes a carbon dioxide sensor for receiving said output optical signal and generating at least one return optical signal representing a carbon dioxide pressure in a sample.

16. The apparatus of claim 1, wherein said second optical channel means includes a pH sensor for receiving said output optical signal and generating at least one return optical signal representing pH of a sample.

17. The apparatus of claim 1, wherein said second optical channel means includes a plurality of return channels in optical communication with said optical interface block for carrying return optical signals, and signal detector means in optical communication with said optical interface block for measuring intensity of said return optical signals.

18. The apparatus of claim 1, wherein said second optical channel means includes signal detector means in optical communication with said optical interface block for measuring intensity of said output optical signal.

19. The apparatus of claim 1, wherein said optical interface block includes a plurality of filter means for receiving said optical signal and transmitting a plurality of output optical signals with different wavelength ranges, and means for combining said plurality of output optical signals.

20. The apparatus of claim 19, wherein said means for combining includes dichroic mirror means.

21. The apparatus of claim 19, wherein said second optical channel means includes a return channel in optical communication with said optical interface block for carrying a return optical signal, and signal detector means in optical communication with said optical interface block for measuring intensity of said return optical signal.

22. The apparatus of claim 19, wherein said optical interface block is in optical communication with an output channel for carrying said combined output optical signals, and includes lens means for focusing said plurality of output optical signals on said output channel means.

23. An optomechanical switching apparatus for use in a system utilizing optical signals, comprising:
  an light source for producing an optical signal;
  rotatable mirror means for directing said optical signal from said light source to a plurality of points located about said mirror means;
  means for controlling the rotational position of the mirror means;
  a plurality of optical fiber channels disposed at said plurality of points about said mirror means adapted to be in optical communication with said mirror means such that as the mirror means is rotated said mirror means is in optical communication with a selected optical fiber channel and the mirror means is not in optical communication with the remaining optical fiber channels; and
  each optical fiber channel being connected to a solid state optical interface block having at least one filter means for receiving said optical signal and transmitting an output optical signal with a limited wavelength range.

24. The apparatus of claim 23 wherein said mirror means is a parabolic mirror for focusing the optical signal onto said selected optical fiber channel.

25. The apparatus of claim 23 wherein said mirror means has an axis of rotation which is normal to a plane in which optical fiber channels are disposed.

26. The apparatus of claim 25 wherein said light source is disposed in the axis of rotation of the mirror.

27. The apparatus of claim 23 wherein said light source is a flashlamp.

28. A method for measuring the concentration of at least one analyte in a sample utilizing an optical signal transmission and detection system having optical fiber analyte sensor means adapted to receive at least one optical excitation signal and adapted to generate at least one output detection signal which is a function of the corresponding analyte concentration in the sample, said analyte sensor means being optically connected through a plurality of corresponding optical channels to an optical signal channel selector apparatus having multiple optical channels for sequentially communicating at least one optical signal, said optical signal channel selector apparatus including at least one first optical channel means for carrying a source optical signal; a plurality of a second optical channel means for carrying said source optical signal, each said second optical channel means including a solid-state optical fiber block having at least one filter means for receiving said source optical signal and transmitting an excitation optical signal with a limited wavelength range to said sensor means; movable selector means adapted to be in optical communication with any one of said first optical channel means and movable to be in optical communication with any one of said second optical channel means for providing optical communication between one of said first optical channel means and a selected second optical channel means; and means for moving said selector means to provide optical communication between one of said first optical channel means and a different one of said second optical channel means, said method comprising the steps of:

a) exposing said optical sensor means to said sample;

b) generating a source optical signal and transmitting said source optical signal from said first optical channel means through said movable selector means to a first one of said second optical channel means to transmit one said excitation optical signal with a limited wavelength range to said sensor means;

c) generating a first said output detection signal responsive to said excitation optical signal;

d) measuring said first output detection signal from said optical sensor means;

e) moving said selector means to transmit said source optical signal from said first optical channel means to a second one of said second optical channel means to transmit a second said excitation optical signal with a limited wavelength range to said optical sensor means;

f) generating a second said output detection signal responsive to said second excitation optical signal;

g) measuring said second output detection signal from said optical sensor means; and h) determining the concentration of at least one analyte in said sample based upon at least one of said first and second output detection signals.

29. The method of claim 28, wherein said selector means comprises mirror means rotatable about an axis and further including the step of controlling a rotational position about said axis to communicate said optical signal between said first optical channel means and sequential ones of said second optical channel means.

30. The method of claim 29, wherein said means for moving said selector means includes a stepper motor having a rotatably driven shaft coaxial with the rotational axis of said mirror means and connected to said mirror means for aligning said mirror means with said sequential ones of said second optical channel means, and said step of controlling said rotational position includes generating an encoded signal representing the rotational position of said mirror means about said axis.

31. The method of claim 28, wherein said optical sensor means comprises a dual emission sensor, and said step of generating at least one output detection signal comprises generating two different output detection signals representing the concentration of the analyte to be measured in the sample.

32. The method of claim 31, wherein said dual emission sensor is an oxygen sensor, and said step of generating at least one output detection signal comprises generating two different output detection signals representing the partial pressure of oxygen in the sample.

33. The method of claim 28, wherein said optical sensor means comprises a dual excitation sensor, and said step of generating an output detection signal comprises generating at least one output detection signal representing the concentration of the analyte to be measured in the sample.

34. The method of claim 33, wherein said dual excitation sensor is a carbon dioxide sensor, and said step of generating an output detection signal comprises generating at least one output detection signal representing a carbon dioxide pressure in the sample.

35. The method of claim 33, wherein said dual excitation sensor is a pH sensor, and said step of generating an output detection signal comprises generating at least one output detection signal representing pH of the sample.

* * * * *